United States Patent
Song et al.

(10) Patent No.: US 11,795,484 B2
(45) Date of Patent: Oct. 24, 2023

(54) **METHOD FOR PREPARING CRUDE POLYSACCHARIDE BASED ON FERMENTATION OF CORN STOVER AND DRIED BEAN CURD RESIDUE BY *CORDYCEPS MILITARIS***

(71) Applicant: Tianjin University, Tianjin (CN)

(72) Inventors: Yingjin Song, Tianjin (CN); Guanyi Chen, Tianjin (CN); Lei Zhong, Tianjin (CN); Yingxiu Zhang, Tianjin (CN); Fawei Lin, Tianjin (CN); Caiyu Wang, Tianjin (CN); Shuyan Meng, Tianjin (CN)

(73) Assignee: TIANJIN UNIVERSITY, Tianjin (CN)

(*) Notice: Subject to any disclaimer, the term of this patent is extended or adjusted under 35 U.S.C. 154(b) by 75 days.

(21) Appl. No.: 17/059,395

(22) PCT Filed: Apr. 29, 2020

(86) PCT No.: PCT/CN2020/087704
§ 371 (c)(1),
(2) Date: Nov. 27, 2020

(87) PCT Pub. No.: WO2020/221282
PCT Pub. Date: Nov. 5, 2020

(65) Prior Publication Data
US 2021/0403966 A1 Dec. 30, 2021

(30) Foreign Application Priority Data
Apr. 29, 2019 (CN) .......................... 201910352105.6

(51) Int. Cl.
*C12P 19/04* (2006.01)
*C12R 1/645* (2006.01)

(52) U.S. Cl.
CPC ........ *C12P 19/04* (2013.01); *C12R 2001/645* (2021.05)

(58) Field of Classification Search
None
See application file for complete search history.

(56) References Cited

FOREIGN PATENT DOCUMENTS

| CN | 101643759 | | 2/2010 |
|----|-----------|---|--------|
| CN | 101643759 | A * | 2/2010 |
| CN | 108522800 | | 9/2018 |
| CN | 110117627 | | 8/2019 |

OTHER PUBLICATIONS

CN 101643759 A, Feb. 10, 2010. English language machine translation. (Year: 2010).*
CN108522800. Sep. 14, 2018. English language machine translation. (Year: 2018).*
CN101643759. Feb. 10, 2010, English language machine translation. (Year: 2010).*
Mani et al. International Journal of Applied Science and Engineering Research (2015), 4(5), 609-619 (Year: 2015).*
International Search Report dated Jul. 29, 2020 for PCT application No. PCT/CN2020/087704.

* cited by examiner

*Primary Examiner* — Christian L Fronda
(74) *Attorney, Agent, or Firm* — WCF IP

(57) ABSTRACT

The application discloses a method for preparing crude polysaccharides based on synergistic fermentation with corn stover and fungus, including the following steps: step (1): drying corn stover, pulverizing, placing in a hydrothermal reactor, adding deionized water, sealing the hydrothermal reactor, placing in a heating device, reacting, taking out reaction products, centrifuging and drying a solid; step (2): adding the products obtained in step (1) and dried bean curd residue to a container, adding distilled water, mixing uniformly, sterilizing to obtain a mixed material, inoculating a fungus inoculum under aseptic conditions, sealing the container and cultivating in the dark to obtain crude polysaccharides. The disclosure uses corn stover and bean curd residue as raw materials to achieve efficient utilization of discarded biomass, reduce environmental pollution, and improve utilization of corn stover.

6 Claims, No Drawings

METHOD FOR PREPARING CRUDE POLYSACCHARIDE BASED ON FERMENTATION OF CORN STOVER AND DRIED BEAN CURD RESIDUE BY *CORDYCEPS MILITARIS*

CROSS-REFERENCE TO RELATED APPLICATIONS

The present application is a Rule 371 filing from PCT/CN2020/087704 filed Apr. 29, 2020, which claims priority of Chinese patent application no. 201910352105.6 filed to the China National Intellectual Property Administration on Apr. 29, 2019 and entitled "METHOD FOR PREPARING CRUDE POLYSACCHARIDES BASED ON SYNERGISTIC FERMENTATION WITH CORN STOVER AND FUNGUS", which is incorporated herein by reference in its entirety.

TECHNICAL FIELD

The disclosure relates to the technical fields of microorganism and fermentation engineering, and in particular to a method for preparing crude polysaccharides based on synergistic fermentation with corn stover and fungus.

BACKGROUND

China has an annual production of about 260 million tons of corn stover. At present, the corn stover is turned into useful resources based on a lot of researches. However, the current technologies are not mature in certain aspects, and a large number of corn stovers still have to be burned, causing environmental pollution and waste of resources. Up to now, an effective utilization rate of corn stover is about 50%. The corn stover is rich in lignocellulose including 25%-35% of cellulose, 20%-40% of hemicellulose, and 10%-25% of lignin. Moreover, the lignin and the hemicellulose which are covalently bonded enclose cellulose molecules, protecting the polysaccharide in cell wall from degradation. A hydrothermal process releases $H^+$ and $OH^-$ from water at a high temperature and a high pressure, which can degrade part of the cellulose, the hemicellulose and the lignin in biomass materials, increasing porosity without adding chemical reagents. Thus, it is an environmentally friendly and pollution-free pretreatment method. Consequently, hydrothermal pretreatment of the corn stover can improve contact of the lignocellulose, thereby improving subsequent utilization of the corn stover.

Solid state fermentation with fungus using biomass substrates as carbon source can effectively degrade and utilize nutrients and produce flavonoids, polyphenols and polysaccharides and the like. A large number of studies have shown that, the solid state fermentation products can have a wide range of significant immune activities, such as promoting body immune function, anti-aging, anti-fatigue, anti-tumor, anti-mutation, reducing blood lipid and preventing mutation. Solid state fermentation with corn stover and fungus can produce crude polysaccharides, where the solid state fermentation can improve a content of produced crude polysaccharides, and the corn stover can be used as a feed, which is green and environment-friendly without secondary pollution. Moreover, the crude polysaccharides are extracted with antioxidant activity fully understood to provide a new antioxidant. As such, the corn stover and products thereof can be used efficiently.

At present, there is no report of producing crude polysaccharides through solid state fermentation with corn stover and bean curd residue by *Cordyceps militaris* or *Phellinus igniarius*.

SUMMARY

The disclosure aims to provide a method for preparing crude polysaccharides based on synergistic fermentation with corn stover and fungus, which is environmentally friendly, pollution-free and easy to operate. The method of the disclosure can achieve efficient utilization of the corn stover from various aspects.

The disclosure provides the following technical solutions.

A method for preparing crude polysaccharides based on synergistic fermentation with corn stover and fungus includes the following steps:

step (1): drying corn stover, pulverizing, screening through a 40-mesh sieve, placing in a hydrothermal reactor, adding deionized water 10-12 times the mass of the corn stover, sealing the hydrothermal reactor, placing in a heating device, heating to 170-190° C. to allow reaction for 10-30 min, taking out the hydrothermal reactor, cooling to room temperature, taking out reaction products, centrifuging and drying a solid to obtain hydrothermal reaction products;

step (2): based on mass, adding 1-2 parts of the hydrothermal reaction products obtained in step (1) and 1-3 parts by mass of dried bean curd residue to a container, adding distilled water to adjust a water content to 65%-75%, mixing uniformly, sterilizing to obtain a mixed material, inoculating a fungus inoculum to the mixed material under aseptic conditions, sealing the container and placing in a fermentation incubator at 23° C. in the dark for 30-35 d to obtain crude polysaccharides.

A ratio of the mixed material to the fungus inoculum is preferably 100 mg:10 ml.

The fungus inoculum is preferably a *Cordyceps militaris* inoculum or a *Phellinus igniarius* inoculum.

The *Cordyceps militaris* inoculum is prepared by a method including the following steps:

step (A): inoculating *Cordyceps militaris* on a potato dextrose agar (PDA) solid medium under aseptic conditions, placing in an incubator at 22-25° C. for 7-9 d to obtain a culture, inoculating the culture on the PDA solid medium and placing in an incubator at 22-25° C. for 7-9 d to obtain a fungus mass;

step (B): inoculating the fungus mass obtained in the step (A) into a first liquid culture medium, placing in a thermostatic culture shaker, and cultivating to mature at 20° C. and 150 r/min in the dark to obtain the *Cordyceps militaris* inoculum;

where the first liquid culture medium has a composition as follows: 30 g of soluble starch, 10 g of glucose, 10 g of peptone, 2 g of potassium dihydrogen phosphate, 2 g of magnesium sulfate, and 10 mg of vitamin B1I, added with water to 1,000 mL, pH=6.5.

The *Phellinus igniarius* inoculum is prepared by a method including the following steps:

step (a): inoculating *Phellinus igniarius* on a PDA solid medium under aseptic conditions and placing in an incubator at 27° C. until the medium is fully covered by hyphae to obtain a fungus mass;

step (b): inoculating the fungus mass obtained in step (b) into a second liquid culture medium, placing in a thermostatic incubator, cultivating at 24-26° C. for 47-49 h, placing in a thermostatic culture shaker, and cultivating at 25° C. and 150 r/min until fungus pellets uniformly appear to obtain the *Phellinus igniarius* inoculum;

where the second liquid culture medium has a composition as follows: 3% of glucose, 0.3% of peptone, 0.1% of $KH_2PO_4$, 0.05% of $MgSO_4$, and water as balance, with a natural pH.

The PDA solid medium includes preferably 3.0 g/L of $KH_2PO_4$, 20.0 g/L of glucose, 1.5 g/L of $MgSO_4$ $7H_2O$, 20.0 g/L of agar, 4.0 g/L of potato extract, and water as balance.

Advantages of the disclosure:
1. The disclosure uses corn stover and bean curd residue as raw materials to achieve efficient utilization of discarded biomass, reduce environmental pollution, and improve utilization of corn stover.
2. The disclosure proposes hydrothermal pretreatment of corn stover, which features easy operation, low investment, and environmental protection.
3. The disclosure uses fungus in solid state fermentation with corn stover to produce crude polysaccharides which is environmentally friendly and pollution-free. The obtained crude polysaccharides have a wide range of uses, for example, use as a feed or an antioxidant.

DETAILED DESCRIPTION

Potato dextrose agar (PDA) solid medium: 3.0 g/L of $KH_2PO_4$, 20.0 g/L of glucose, 1.5 g/L of $MgSO_4$ $7H_2O$, 20.0 g/L of agar, 4.0 g/L of potato extract, and water as balance.

A first liquid culture medium has a formula as follows: 30 g of soluble starch, 10 g of glucose, 10 g of peptone, 2 g of potassium dihydrogen phosphate, 2 g of magnesium sulfate, and 10 mg of vitamin B1, added with water to 1,000 mL, pH=6.5.

A second liquid culture medium has a formula as follows: 3% of glucose, 0.3% of peptone, 0.1% of $KH_2PO_4$, 0.05% of $MgSO_4$, and water as balance, with a natural pH.

The disclosure will be further described below with reference to specific examples. The following examples are provided to facilitate better understanding of the disclosure by those skilled in the art, but they do not limit the disclosure in any way.

*Cordyceps militaris* and *Phellinus igniarius* are purchased from the company Beina Bio.

Example 1

A *Cordyceps militaris* inoculum was prepared by a method including the following steps:
Step (1): *Cordyceps militaris* was inoculated on the PDA solid medium under aseptic conditions, placed in an incubator at 23° C. for 8 d. An obtained culture was inoculated on the PDA solid medium and placed in an incubator at 23° C. for 8 d.
Step (2): A fungus mass obtained in step (1) was inoculated into the first liquid culture medium, placed in a thermostatic culture shaker, and cultivated to mature at 20° C. and 150 r/min in the dark to obtain a *Cordyceps militaris* inoculum.

Example 2

A *Cordyceps militaris* inoculum was prepared by a method including the following steps:
Step (1): *Cordyceps militaris* was inoculated on the PDA solid medium under aseptic conditions, placed in an incubator at 22° C. for 9 d. An obtained culture was inoculated on the PDA solid medium and placed in an incubator at 22° C. for 9 d.
Step (2): A fungus mass obtained in step (1) was inoculated into the first liquid culture medium, placed in a thermostatic culture shaker, and cultivated to mature at 20° C. and 150 r/min in the dark to obtain a *Cordyceps militaris* inoculum.

Example 3

A *Cordyceps militaris* inoculum was prepared by a method including the following steps:
Step (1): *Cordyceps militaris* was inoculated on the PDA solid medium under aseptic conditions, placed in an incubator at 25° C. for 7 d. An obtained culture was inoculated on the PDA solid medium and placed in an incubator at 25° C. for 7 d.
Step (2): A fungus mass obtained in step (1) was inoculated into the first liquid culture medium, placed in a thermostatic culture shaker, and cultivated to mature at 20° C. and 150 r/min in the dark to obtain a *Cordyceps militaris* inoculum.

Example 4

A *Phellinus igniarius* inoculum was prepared by a method including the following steps:
Step (1): *Phellinus igniarius* was inoculated on the PDA solid medium under aseptic conditions and placed in an incubator at 27° C. until the medium was fully covered by hyphae.
Step (2): A fungus mass obtained in step (1) was inoculated into the second liquid culture medium, placed in a thermostatic incubator, cultivated at 25° C. for 48 h, placed in a thermostatic culture shaker, and cultivated at 25° C. and 150 r/min until fungus pellets uniformly appeared to obtain a *Phellinus igniarius* inoculum.

Example 5

A *Phellinus igniarius* inoculum was prepared by a method including the following steps:
Step (1): *Phellinus igniarius* was inoculated on the PDA solid medium under aseptic conditions and placed in an incubator at 27° C. until the medium was fully covered by hyphae.
Step (2): A fungus mass obtained in step (1) was inoculated into the second liquid culture medium, placed in a thermostatic incubator, cultivated at 24° C. for 49 h, placed in a thermostatic culture shaker, and cultivated at 25° C. and 150 r/min until fungus pellets uniformly appeared to obtain a *Phellinus igniarius* inoculum.

Example 6

A *Phellinus igniarius* inoculum was prepared by a method including the following steps:
Step (1): *Phellinus igniarius* was inoculated on the PDA solid medium under aseptic conditions and placed in an incubator at 27° C. until the medium was fully covered by hyphae.
Step (2): A fungus mass obtained in step (1) was inoculated into the second liquid culture medium, placed in a thermostatic incubator, cultivated at 26° C. for 47 h, placed in a thermostatic culture shaker, and cultivated at 25° C. and 150 r/min until fungus pellets uniformly appeared to obtain a *Phellinus igniarius* inoculum.

Example 7

A method for preparing crude polysaccharides based on synergistic fermentation with corn stover and fungus included the following steps:

Step (1): corn stovers were dried, pulverized, screen through a 40-mesh sieve, and placed in a hydrothermal reactor. Deionized water 11 times the mass of the corn stovers was added. The hydrothermal reactor was sealed, placed in a heating device, and heated to 180° C. to allow reaction for 20 min. The hydrothermal reactor was taken out and cooled to room temperature. Reaction products were taken out and centrifuged. A solid was dried.

Step (2): based on mass, a container was added with 1.5 parts of the products obtained in step (1) and 2 parts of dried bean curd residue. Distilled water was added to adjust a water content to 70%. Uniform mixing and sterilization was carried out to obtain a mixed material. The *Cordyceps militaris* inoculum prepared in Example 1 was inoculated under aseptic conditions. Then the container was sealed and placed in a fermentation incubator at 23° C. in the dark for 33 d to obtain crude polysaccharides.

A ratio of the mixed material to the Cordyceps militaris inoculum was 100 mg:10 ml.

A content of the crude polysaccharides was measured to be 0.4651 mg/g.

Example 8

A method for preparing crude polysaccharides based on synergistic fermentation with corn stover and fungus included the following steps:

Step (1): corn stovers were dried, pulverized, screen through a 40-mesh sieve, and placed in a hydrothermal reactor. Deionized water 10 times the mass of the corn stovers was added. The hydrothermal reactor was sealed, placed in a heating device, and heated to 170° C. to allow reaction for 30 min. The hydrothermal reactor was taken out and cooled to room temperature. Reaction products were taken out and centrifuged. A solid was dried.

Step (2): based on mass, a container was added with 1 part of the products obtained in step (1) and 1 part of dried bean curd residue. Distilled water was added to adjust a water content to 65%. Uniform mixing and sterilization was carried out to obtain a mixed material. The *Cordyceps militaris* inoculum prepared in Example 2 was inoculated under aseptic conditions. Then the container was sealed and placed in a fermentation incubator at 23° C. in the dark for 30 d to obtain crude polysaccharides.

A ratio of the mixed material to fungus inoculum was preferably 100 mg:10 ml.

A content of the crude polysaccharides was measured to be 0.3730 mg/g.

Example 9

A method for preparing crude polysaccharides based on synergistic fermentation with corn stover and fungus included the following steps:

Step (1): corn stovers were dried, pulverized, screen through a 40-mesh sieve, and placed in a hydrothermal reactor. Deionized water 12 times the mass of the corn stovers was added. The hydrothermal reactor was sealed, placed in a heating device, and heated to 190° C. to allow reaction for 10 min. The hydrothermal reactor was taken out and cooled to room temperature. Reaction products were taken out and centrifuged. A solid was dried.

Step (2): based on mass, a container was added with 2 parts of the products obtained in step (1) and 3 parts of dried bean curd residue. Distilled water was added to adjust a water content to 75%. Uniform mixing and sterilization was carried out to obtain a mixed material. The *Cordyceps militaris* inoculum prepared in Example 3 was inoculated under aseptic conditions. Then the container was sealed and placed in a fermentation incubator at 23° C. in the dark for 35 d to obtain crude polysaccharides.

A ratio of the mixed material to fungus inoculum was preferably 100 mg:10 ml.

A content of the crude polysaccharides was measured to be 0.3728 mg/g.

Example 10

A method for preparing crude polysaccharides based on synergistic fermentation with corn stover and fungus included the following steps:

The *Phellinus igniarius* inoculum prepared in Example 4 was used to replace the *Cordyceps militaris* inoculum in Example 7, and the other operations were the same as those in Example 7 to obtain crude polysaccharides.

A content of the crude polysaccharides was measured to be 0.3729 mg/g.

Example 11

A method for preparing crude polysaccharides based on synergistic fermentation with corn stover and fungus included the following steps:

The *Phellinus igniarius* inoculum prepared in Example 5 was used to replace the *Cordyceps militaris* inoculum in Example 8, and the other operations were the same as those in Example 8 to obtain crude polysaccharides.

A content of the crude polysaccharides was measured to be 0.3812 mg/g.

Example 12

A method for preparing crude polysaccharides based on synergistic fermentation with corn stover and fungus included the following steps:

The *Phellinus igniarius* inoculum prepared in Example 6 was used to replace the *Cordyceps militaris* inoculum in Example 9, and the other operations were the same as those in Example 9 to obtain crude polysaccharides.

A content of the crude polysaccharides was measured to be 0.3888 mg/g.

The above contents cannot be recognized as that the specific embodiments of the disclosure are only limited to these descriptions. All equivalent changes and modifications made within the scope of the disclosure should fall within the scope of disclosure determined by the claims submitted in the disclosure.

What is claimed is:

1. A method for preparing crude polysaccharides based on fermentation of corn stover and dried bean curd residue by *Cordyceps militaris*, comprising the following steps:
   - step (1): drying corn stover, pulverizing, screening through a 40-mesh sieve, placing in a hydrothermal reactor, adding deionized water 10-12 times the mass of the corn stover, sealing the hydrothermal reactor, placing in a heating device, heating to 170-190° C. to allow reaction for 10-30 min, taking out the hydrothermal reactor, cooling to room temperature, taking out reaction products, centrifuging and drying a solid to obtain hydrothermal reaction products;
   - step (2): based on mass, adding 1-2 parts of the hydrothermal reaction products obtained in step (1) and 1-3 parts by mass of dried bean curd residue to a container, adding distilled water to adjust a water content to 65%-75%, mixing uniformly, sterilizing to obtain a mixed material, inoculating *Cordyceps militaris* inoculum to the mixed material under aseptic conditions, sealing the container and placing in a fermentation incubator at 23° C. in the dark for 30-35 d to obtain crude polysaccharides.

2. The method according to claim 1, wherein a ratio of the mixed material to the *Cordyceps militaris* inoculum is 100 mg:10 ml.

3. The method according to claim 1, wherein the *Cordyceps militaris* inoculum is prepared by a method comprising the following steps:
   - step (A): inoculating Cordyceps militaris on a potato dextrose agar (PDA) solid medium under aseptic conditions, placing in an incubator at 22-25° C. for 7-9 d to obtain a culture, inoculating the culture on the PDA solid medium and placing in an incubator at 22-25° C. for 7-9 d to obtain a fungus mass;
   - step (B): inoculating the fungus mass obtained in the step (A) into a first liquid culture medium, placing in a thermostatic culture shaker, and cultivating to mature at 20° C. and 150 r/min in the dark to obtain the *Cordyceps militaris* inoculum;

wherein the first liquid culture medium has a composition as follows: 30 g of soluble starch, 10 g of glucose, 10 g of peptone, 2 g of potassium dihydrogen phosphate, 2 g of magnesium sulfate, and 10 mg of vitamin B 1, added with water to 1,000 mL, pH=6.5.

4. The method according to claim 3, wherein the PDA solid medium comprises 3.0 g/L of $KH_2PO_4$, 20.0 g/L of glucose, 1.5 g/L of $MgSO_4$ $7H_2O$, 20.0 g/L of agar, 4.0 g/L of potato extract, and water as balance.

5. The method according to claim 2, wherein the *Cordyceps militaris* inoculum is prepared by a method comprising the following steps:
   - step (A): inoculating *Cordyceps militaris* on a potato dextrose agar (PDA) solid medium under aseptic conditions, placing in an incubator at 22-25° C. for 7-9 d to obtain a culture, inoculating the culture on the PDA solid medium and placing in an incubator at 22-25° C. for 7-9 d to obtain a fungus mass;
   - step (B): inoculating the fungus mass obtained in the step (A) into a first liquid culture medium, placing in a thermostatic culture shaker, and cultivating to mature at 20° C. and 150 r/min in the dark to obtain the *Cordyceps militaris* inoculum;

wherein the first liquid culture medium has a composition as follows: 30 g of soluble starch, 10 g of glucose, 10 g of peptone, 2 g of potassium dihydrogen phosphate, 2 g of magnesium sulfate, and 10 mg of vitamin B 1, added with water to 1,000 mL, pH=6.5.

6. The method according to claim 2, wherein the PDA solid medium comprises 3.0 g/L of $KH_2PO_4$, 20.0 g/L of glucose, 1.5 g/L of $MgSO_4$ $7H_2O$, 20.0 g/L of agar, 4.0 g/L of potato extract, and water as balance.

* * * * *